United States Patent [19]

Miripol et al.

[11] Patent Number: 4,952,812
[45] Date of Patent: Aug. 28, 1990

[54] IRRADIATION OF BLOOD PRODUCTS

[75] Inventors: Jeffrey E. Miripol, Newark, Del.; Arnold Bilstad, Deerfield, Ill.; John Foley, Wheeling, Ill.; Dean Glash, McHenry, Ill.; William R. Bratten, Lake Villa, Ill.

[73] Assignee: Baxter International Inc., Deerfield, Ill.

[21] Appl. No.: 346,202

[22] Filed: May 2, 1989

Related U.S. Application Data

[60] Continuation-in-part of Ser. No. 156,637, Feb. 17, 1988, Pat. No. 4,866,282, which is a division of Ser. No. 900,217, Aug. 26, 1986, abandoned.

[51] Int. Cl.$^5$ .............................................. A61N 5/06
[52] U.S. Cl. .............................. 250/455.1; 250/454.1; 250/492.1; 422/24
[58] Field of Search ..................... 250/455.1, 432 R; 128/804; 604/4, 6; 424/101, 89

[56] References Cited

U.S. PATENT DOCUMENTS

| | | |
|---|---|---|
| 2,001,555 | 5/1935 | Trebler . |
| 4,048,504 | 9/1977 | Bosshard . |
| 4,398,906 | 8/1983 | Edelson . |
| 4,433,244 | 2/1984 | Hogan ............................. 250/455.1 |
| 4,448,750 | 5/1984 | Fuesting ......................... 250/455.1 |
| 4,487,870 | 12/1984 | Bartz . |
| 4,540,573 | 9/1985 | Neurath et al. ................... 424/101 |
| 4,590,124 | 5/1986 | Schoenberg . |
| 4,608,255 | 8/1986 | Kahn et al. . |
| 4,612,007 | 9/1986 | Edelson . |
| 4,613,501 | 9/1986 | Horowitz ............................ 424/89 |
| 4,705,498 | 11/1987 | Goss ................................. 604/6 |
| 4,708,715 | 11/1987 | Troutner et al. .................... 604/6 |
| 4,737,140 | 4/1988 | Lee et al. ........................... 604/4 |
| 4,764,369 | 8/1988 | Neurath et al. ..................... 424/89 |
| 4,801,427 | 1/1989 | Jacob ............................. 250/455.1 |
| 4,820,805 | 4/1989 | Neurath et al. ..................... 424/89 |
| 4,878,891 | 11/1989 | Judy et al. ........................ 424/101 |

OTHER PUBLICATIONS

Bredberg et al.—Chemical Abstracts, vol. 101 (1984) p. 146941h.
Lagner et al.—Chemical Abstracts, vol. 88 (1978) p. 31915y.
Lynch et al.—Chemical Abstracts, vol. 99 (1983) p. 172086t.
Krylenkov et al.—Chemical Abstracts, vol. 101 (1984) p. 206812d.

Primary Examiner—Janice A. Howell
Assistant Examiner—Kiet T. Nguyen
Attorney, Agent, or Firm—Paul C. Flattery; Garrettson Ellis; Bradford R. L. Price

[57] ABSTRACT

A thin film or layer of white blood cells, such as the contaminating white cells in a platelet concentrate, is irradiated with ultraviolet radiation predominately of a wavelength of 280 to 320 nanometers, and preferably at an intensity of 4 to 20 milliwatts per square cm. to provide a total energy exposure of typically 800 to 20,000 millijoules per square cm. of ultraviolet radiation. The white blood cells so produced substantially lose their capability to set off an immune reaction in an alloimmunized patient. The white blood cells may preferably be placed into such film in a flat, flexible bag made of poly(ethylene-vinyl acetate) plastic, with the flat, flexible bag being stretched in a direction normal to the path of ultraviolet radiation. Novel irradiating devices are also disclosed.

31 Claims, 2 Drawing Sheets

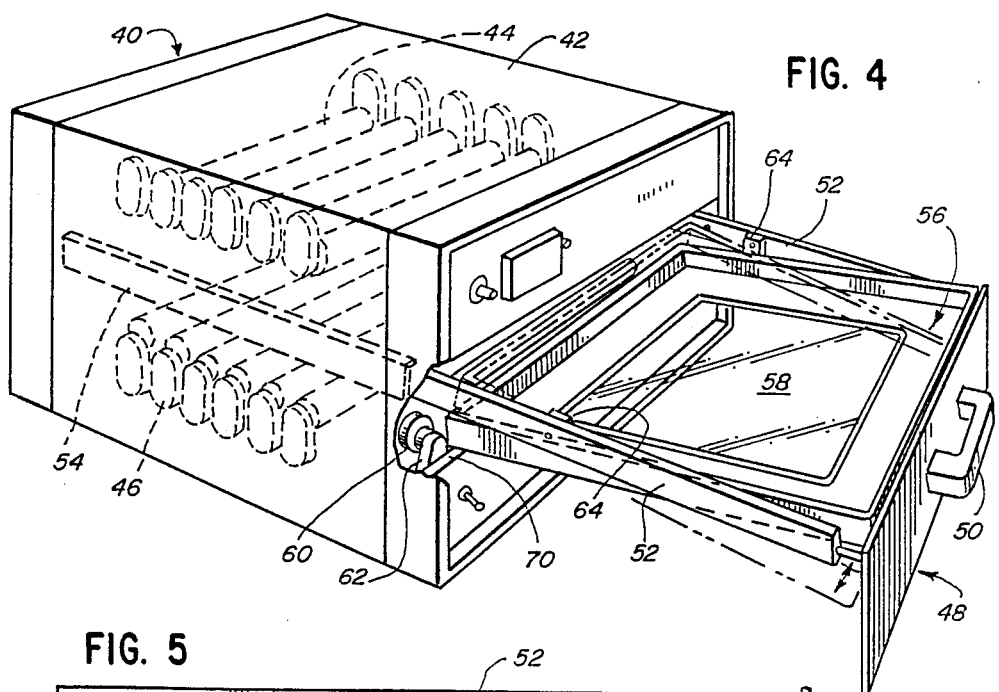
FIG. 4
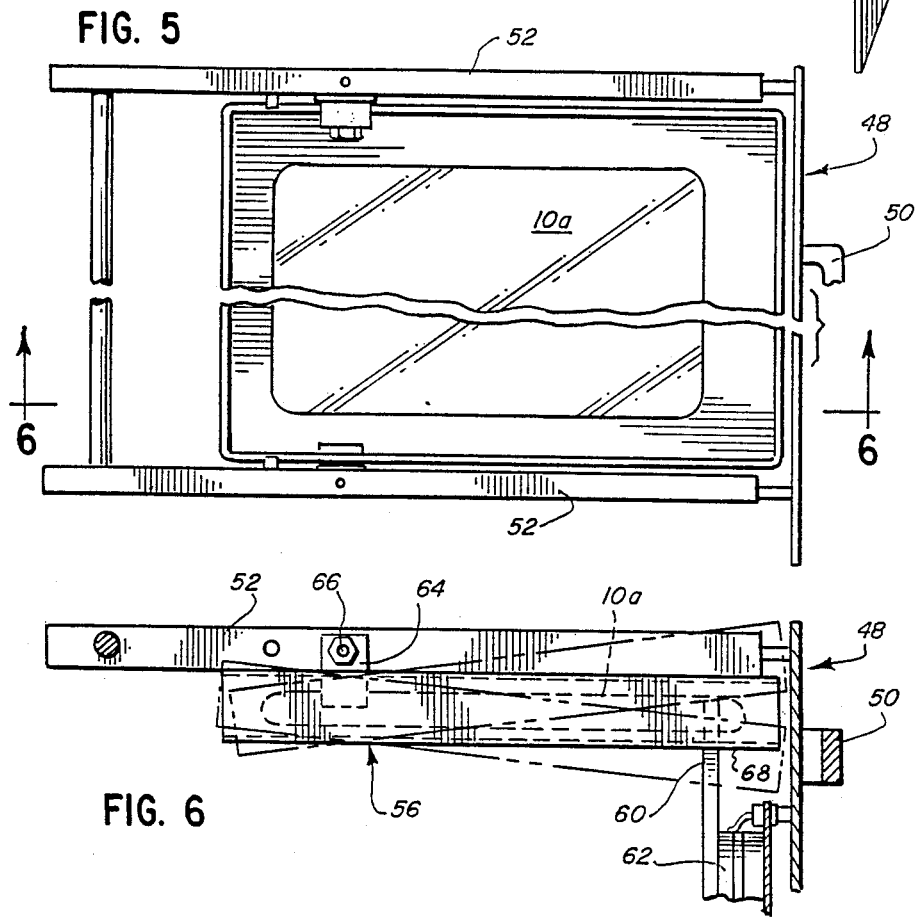
FIG. 5
FIG. 6

IRRADIATION OF BLOOD PRODUCTS

REFERENCE TO RELATED APPLICATION

This is a continuation-in-part of U.S. patent application Ser. No. 156,637, filed Feb. 17, 1988, now U.S. Pat. No. 4,866,282, which in turn, is a division of U.S. patent application Ser. No. 900,217, filed Aug. 26, 1986, now U.S. Pat. No. 4,726,949.

TECHNICAL FIELD

In Kahn U.S. Pat. No. 4,608,255, entitled: A Biocompatible Container and Method for In Situ Production of Functional Platelets Lacking in Immunogenicity, it is taught to expose platelet preparations to ultraviolet (U.V.) radiation, to eliminate or greatly decrease an immune response to the platelet preparation by alloimmunized patients. As observed by Dr. Kahn, it is generally believed that this alloimmunization is caused by the passenger lymphocytes present in the platelet concentrates prepared by a standard procedure.

The effect of such an alloimmunization reaction is that donated platelets are quickly removed from the bloodstream of a patient, so that the beneficial, life saving effect of administered platelets may eventually become unavailable to patients in serious need of it, despite frequent infusions of platelets to such a patient.

As taught by Dr. Kahn, the alloimmunization of a patient comes from repeated platelet transfusions, as may be necessary for cancer patients undergoing chemotherapy or the like.

The Kahn patent application teaches placing a platelet suspension in a plastic container which is permeable to ultraviolet radiation. Specifically, a dosage of radiation of about 645 Joules per square meter for about 10 to 40 minutes is proposed, using polyethylene, polypropylene, or polyvinyl chloride bags. The ultraviolet radiation passes through the bag walls to irradiate platelets and other cells present, to provide a cell preparation for administration to a patient which elicits little or no immune response from patients who have been alloimmunized to such platelet preparations.

While the Kahn method restores to alloimmunized patients the life saving benefits of platelet therapy, certain disadvantages are found. In the actual work of Kahn upon which the Kahn patent application was based, it has turned out to be necessary or at least highly desirable to agitate the platelet preparation while they are being irradiated. Otherwise, incomplete results are achieved. Additionally, while Kahn suggests the use of several different plastic materials for use in his cell irradiation process, one particular plastic formulation provides additional advantages above and beyond the teachings of Kahn, when used in accordance with this present application.

Accordingly, the improvements provided by the invention of this application produce a significantly improved method for treating white blood cells so as to permit their effective use in alloimmunized patients. Specifically, agitation of the cells during irradiation is not required, but may be preferred. A superior, U.V. "B" transparent bag material is provided, and the blood cell preparations may be irradiated for shorter periods of time, while achieving substantially equal benefits to those provided by the process of Dr. Kahn.

DESCRIPTION OF THE INVENTION

In accordance with this invention, a layer or thin film of blood product, such as platelet concentrates typically with white cell contamination, is irradiated with ultraviolet radiation predominately of a wavelength of 280 to 320 nanometers and typically at an intensity of 4 to 20 and preferably 10 to 15 milliwatts per square cm., to provide a total energy exposure of typically 800 to 20,000 millijoules per square cm. of ultraviolet radiation, and preferably 1000 to 14,000 millijoules per square cm. As the result of this, the white blood cells present in the blood product substantially lose their capability to set off an immune reaction in an alloimmunized patient. Excessive U.V. energy exposure is generally deleterious to the blood product, while not enough U.V. energy does not reduce the lymphocyte stimulatory activity to a sufficient degree.

In accordance with this invention, the exposure of the blood to ultraviolet radiation of the wavelength and intensity as specified above typically eliminates the need for agitation of the film, although when the cells are gently agitated to mix them during the irradiation process, less radiation exposure is required to accomplish the purpose, and the cells are more uniformly exposed to the radiation. Typically also, the length of the irradiation process may be from 0.25 (preferably 10 minutes) to 30 minutes long, which, due to increased intensity when compared with the Kahn et al. work, provides a shorter processing time.

Preferably, the white blood cells are irradiated while occupying a flat, flexible bag made of poly(ethylenevinyl acetate) plastic. This material is highly transparent to ultraviolet radiation; retains its strength at cryogenic temperatures if the cells are to be stored under cryogenic conditions; is easily fabricated by heat sealing into flat, flexible bags; and exhibits the high oxygen permeability through the bag wall which is desired for a container for storing platelets or the like.

Typically, the layer or thin film of blood product, such as platelet concentrate contaminated with white blood cells, is from 0.1 to 5 cm. thick during the irradiation step, preferably no more than 2 cm. thick. It is also typical for the flat, flexible bag used in this process, and made out of poly(ethylene-vinyl acetate) plastic, to contain from 10 to 30 weight percent of vinyl acetate units, with the balance being ethylene units, such bag preferably having a wall thickness of 0.005 to 0.025 inch.

It is also preferable in accordance with this invention to stretch the flat, flexible bag in at least one direction which is normal to the direction of ultraviolet radiation, to help define the thin film of blood product with the bag.

The term "white blood cells" is intended to include the general class of leukocytes, including mononuclear cells and neutraphils, lymphocytes, and any other cells found in the blood, above and beyond red cells and platelets. It is to be understood that the blood product processed in this invention may, and usually does include. platelets and/or red cells. Also, substantially cell-free products having some white cells may be treated by this invention. Likewise, whole blood may be irradiated in accordance with the invention, or any other fraction thereof.

It is generally desired to use high intensity ultraviolet bulbs, with specific output in the UV-B wavelength range, for the process of this invention. Not all ultraviolet bulbs are capable of providing sufficient intensity for the purposes of this invention. Also, some ultraviolet bulbs emit much energy at a wavelength of 254 nanometers, and are not as effective in providing the desired effect as the somewhat longer wavelength ultraviolet radiation used in this invention. In addition, 254 nanometer energy causes damage to blood cells. Also, bulbs providing energy in the UV-A range (about 365 nonometers) do not provide good reduction of the lymphocyte alloimmunization effect.

Flexible, collapsible bags made of poly(ethylene-vinyl acetate) (E.V.A.) plastic are commercially available from the Fenwal Division of Baxter International of Deerfield, Ill.

As an additional aspect of this invention, apparatus is provided for irradiating with ultraviolet radiation a layer containing white blood cells. The apparatus comprises a housing, and means for providing ultraviolet radiation. Means are also provided for supporting in the housing a layer of white blood cells in a position to be irradiated by the irradiation means, which may typically be a battery of UV bulbs, preferably positioned both above and below the layer of blood product containing white blood cells.

The means for supporting the white blood cell layer comprises a drawer member slidable into and out of the housing, to carry an ultraviolet transmissive container which defines the layer within the container. The drawer member, in turn, defines a container-supporting, ultraviolet-transmissive surface to permit ultraviolet radiation from the untraviolet providing means to pass through the container-supporting surface and the container carried thereon. By this means, the container and its layer of blood product containing white blood cells can be irradiated with ultraviolet through the drawer member and the underside of the container.

Additionally and preferably, the source of ultraviolet radiation also provides such radiation directly to the upper side of the container, facing away from the container-supporting surface, so that ultraviolet irradiates the blood product layer from at least two directions.

Preferably, the container-supporting, ultraviolet-transmissive surface is made of quartz, which can serve to support the bag, but is substantially transparent to ultraviolet radiation, particularly in the prefered UV-B wavelength range.

The container-supporting, ultraviolet-transmissive surface may comprise at least part of a drawer bottom which is pivotally attached to the remainder of the drawer member. The drawer member is movable between an open position permitting placement and removal of the container into and out of the drawer member, and a closed position in which the container in the drawer member is positioned within the housing for ultraviolet irradiation. Elevating means may also be provided in the apparatus, being positioned to cause intermittent, back-and-forth pivoting of the drawer bottom while the drawer member is in its closed position. The effect of this is to permit agitation of the layer containing white blood cells in the ultraviolet-transmissive container simultaneously with ultraviolet irradiation thereof. Typically, the elevating means for causing intermittent, back-and-forth pivoting of the drawer bottom comprises a rotatable, eccentric cam, plus an appropriate motor to power the cam.

DESCRIPTION OF DRAWINGS

In the drawings.

FIG. 4 is a perspective view of another embodiment of an irradiation device in accordance with this invention;

FIG. 5 is a fragmentary, plan view showing details of the drawer member carried in the apparatus of FIG. 4; and FIG. 6 is a sectional view taken along line 6—6 of FIG. 5.

DESCRIPTION OF SPECIFIC EMBODIMENTS

Figure 1:
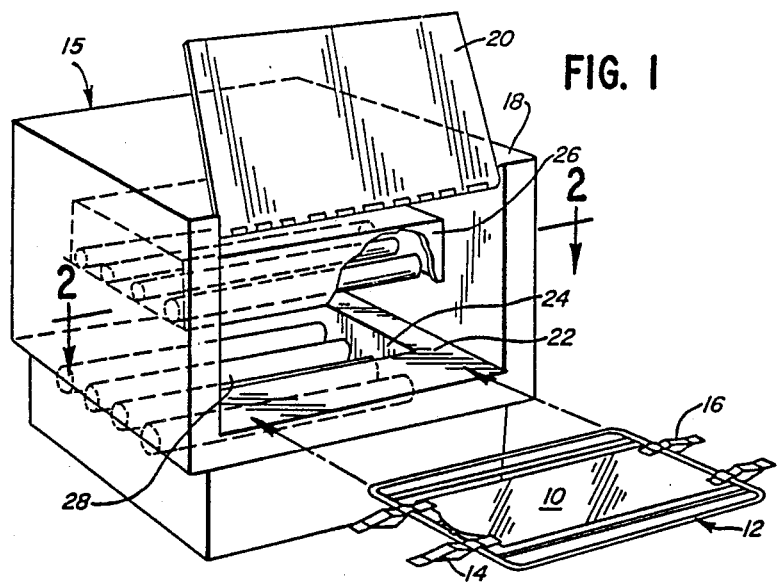
FIG. 1 is a perspective view of an irradiation device which is in the process of receiving a stretched, plastic container of platelets mixed with white blood cells.
Figure 2:
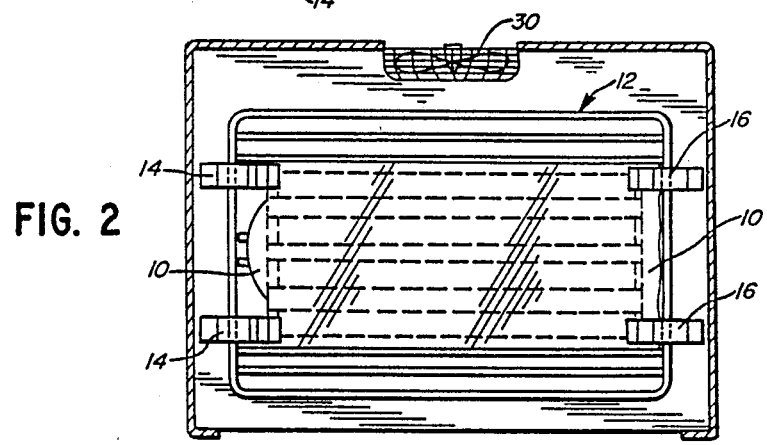
FIG. 2 is a sectional view taken along line 2—2 of FIG. 1, showing the plastic bag carried in its stretching device and positioned for irradiation inside the radiation apparatus.

Referring to FIGS. 1 and 2, a flexible, collapsible bag 10 is provided, holding a unit of platlets which have been collected by conventional oentrifugal processing of freshly collected whole blodd, or by on-line apheresis collection of platelet products.

In FIG. 2, bag 10 is carried upon a framework 12 of metal rods which are welded together at the corners. As shown, the ends of collapsible bag 10 are retained by spring clips 14, 16, to hold the bag in stretched condition. The effect of this is to cause the thickness of the platelet preparation within bag 10 to be minimized, and to be made relatively uniform, so that the dosage of ultraviolet radiation received by the individual portions of the platelet preparation is rather constant. Biaxial stretching of bag 10 may also be used if desired.

U.V. radiation device 15 defines a casing 18, a sliding door 20, and interior rack 22. Rack 22 is provided centrally in the device with an aperture 24, which is preferably sized so that the entire bag 10 may be placed over said aperture, with clips 14, 16, resting upon rack 22 to support bag 10 over aperture 24.

In this particular embodiment, device 15 defines an upper light fixture 26, and lower light fixture 28. The specific lights used, and the electronic circuitry controlling such use, may be entirely conventional, utilizing typically commercially available high intensity bulbs such as eight to twelve bulbs purchased from Spectronics Corp., Westbury, N.Y. (such as model BLE-1T158). Also, exhaust fan 30 may be provided in the back of casing 18 to exhaust the heat generated by bulb assemblies 26, 28.

The device is designed so that platelets (or other blood products treated with this system) do not become heated above 31 degrees C. Prolonged heating of such above 31 degrees C. is deleterious to their function.

In operation, the individual bags 10, typically of platelets (plus a few lymphocytes, which are suspected as being the prime contributors to the alloimmunization process), are stretched in framework 12, and inserted horizontally into ultraviolet application chamber so that bag 10 rests over aperture 24. Sliding door 20 is closed, and the thin film of platelets contaminated with white blood cells within stretched bag 10 is irradiated with ultraviolet radiation, typically with a wavelength of predominately 300 to 320 nanometers, having a maximum emission of about 300–310 nanometers. No means for agitating the bag is necessary in order to achieve the desired purpose of this invention of causing the white blood cells to lose their potential to set off an immune reaction in an alloimmunized patient.

Specifically, the thickness of the film of blood product within bag 10 is about 1–4 cm. thick, typically 2 cm., with a typical bag 10 having a wall thickness of about 0.015 inch, and being made of E.V.A. plastic having about 18 weight percent of vinyl acetate units, the balance being ethylene units. Typically, the intensity of the ultraviolet radiation is about 12 milliwatts per square cm., and the irradiation process may have a duration of about 16 minutes, to provide about 12,000 millijoules per square cm.

After the irradiation step is complete, ultraviolet light assemblies 26, 28, may be shut off; door 20 may be opened; and bag 10 with its attached framework 12 removed. Bag 10 is then easily removed from spring clips 14, 16, and placed under conventional storage conditions until use with a patient is desired. Immediately thereafter, or at any other desired time, another bag 10 may be stretched into framework 12, and the process may be repeated, to provide white blood cells, and especially platelet-containing solutions, which do not set off an alloimmune reaction in patients.

Figure 3:
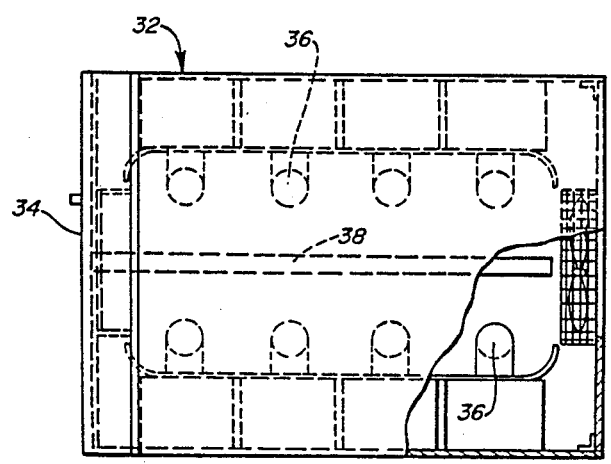
FIG. 3 is a plan view, with portions broken away, of another embodiment of apparatus utilized to perform the method of this application.

Turning to FIG. 3, the plan view of a bag irradiation device is shown, having casing 32 and door 34, into which assemblies of framework 12 and cell-containing bags 10 may be inserted. In this particular design, ultraviolet bulbs 36 may be vertically mounted on both sides of a sliding track 38 into which framework 23 can slidingly be fit and travel into and out of irradiation device 32.

In this embodiment, bag 10 may be placed with its longer axis of width extending vertically, to be parallel to the axes of U.V. bulbs 36, which are of cylindrical shape, shown in cross section in FIG. 3.

Upon installation of framework 12 and bag 10 within the structure of FIG. 3, door 34 may be closed and lights 36 actuated to provide light of 280 to 320 nanometers and at a typical intensity of about 9 to 14 milliwatts per square cm.

No apparatus for agitating the white blood cells within bag 10 is provided in this embodiment either, since it has been found that irradiation at the wavelength and intensity as specified above can provide sufficient irradiation to the blood cells in a stretched bag carrying a unit of such cells, without agitation.

The E.V.A. bags preferably used in this invention have the added desirable feature in that they may be free of leachable materials. This reduces the amount of undesired and uncontrolled materials which find their way into the blood cell preparations during processing.

Continuous ultraviolet irradiation processes may be used as well, with the bags lying on a conveyor belt, either with or without stretching as provided by framework 12, to be carried across a source of ultraviolet radiation. The ultraviolet radiation may come from only one direction, using a single ultraviolet light assembly, or a plurality of such light assemblies may be provided, above or below, and/or from side-to-side of such conveyor belt. Alternatively a series of ultraviolet sources may be provided in-line sequentially to expose the containers to the desired level of ultraviolet radiation.

Additionally, a safety interlock may be provided by conventional means to prevent activation of the ultraviolet lights while the door of either casing 18 or 32 is open. Additionally, electronic circuitry and UV sensors are known for causing the ultraviolet lights to be activated until a desired overall integrated exposure is reached, and then causing the ultraviolet bulbs to shut off when such exposure is reached. Such an exposure control system operates independently of time and intensity, and may be used in this invention if desired.

Alternatively, bag 10 may be squeezed with a U.V.-transparent plate (e.g. quartz), or a screen, rather than stretching, to achieve a uniform, thin film during irradiation.

As another example, an EVA bag of platelet concentrate was irradiated, without agitation, from both sides at a total intensity of 10 to 14 milliwatts per square cm. with UV light at a frequency of primarily 280 to 320 nanometers. An apparatus similar to that shown in the drawings was used to accomplish this. In one instance the thickness of the platelet preparation in the bag was about 0.61 inch (1.55 cm.). For this, a UV irradiation dosage of about 12000 millijoules per square cm. was required to essentially eliminate the alloimmunization reaction capability of the white blood cells present with the platelets. In another instance, the thickness of the platelet preparation in the bag was about 0.56 inch (1.42 cm.). For this, a UV irradiation dosage of about 8250 millijoules per square cm. was required to essentially eliminate the alloimmunization reaction capability.

By way of another example, layers of platelet concentrate were irradiated with UV radiation as described above, but from only a single side and with the platelet concentrate being open and directly exposed to the UV light, not in a bag. During the irradiation, the platelet concentrate was gently agitated to continually mix the cells. The UV light intensity was essentially the same as above.

When the platelet layer thickness was about 0.33 inch (0.84 cm.) a UV irradiation dosage of about 3400 millijoules per square cm. was necessary to essentially eliminate the alloimmunization capability of the white cells present with the platelets. When the platelet layer thickness was about 0.06 inch (0.15 cm.) the corresponding UV irradiation doseage was about 600 millijoules per square cm.

Referring to FIGS. 4 through 6, another design of irradiation device is disclosed, for the ultraviolet irradiation of blood cell-containing bags in a manner similar to those of the previous embodiments. Except as otherwise indicated herein, the apparatus, process, and conditions may be the same as in the previous embodiments.

Irradiating apparatus 40 defines a housing 42 which contains two spaced banks of UV bulbs 44, 46 for providing the desired ultraviolet irradiation, preferably under the conditions of frequency, intensity, and total energy exposure are previously described.

Irradiating apparatus 40 carries a drawer member 48 which defines a front plate and handle 50 attached to an outer frame 52 which slides in conventional manner on both sides of the drawer in a drawer slide 54 within housing 42.

In accordance with this invention, drawer bottom 56, positioned between drawer side members 52 and carried thereby, define a container-supporting, ultraviolet-transmissive surface in the form of a window 58 which is made of an ultraviolet-transmissive material such as quartz. Thus, when drawer 48 is in its open position as shown in FIG. 4, one can lay on drawer bottom 56 a flexible, collapsible bag 10a, similar to the previous bag 10, which contains the desired platelet preparation to be irradiated. Window 58 is large enough so that, typically, the entire bag 10a can be placed thereon, so that ultraviolet irradiation from UV light bank 46 can pass through window 58 and bag 10a to irradiate the platelet preparation when drawer 48 is in the closed position, as shown in fragmentary manner in FIG. 6. At the same time, in the closed position upper bank 44 of UV lights provide direct radiation to bag 10a resting on drawer bottom 56, and its contents.

Thus it becomes an easy manner to simply place a bag for irradiation on the drawer 48, to close the drawer, and to proceed with irradiation, which is provided to the platelet preparation from two sides by the respective UB light banks 44, 46.

Additionally in accordance with this invention, it may be possible to reduce the necessary effective ultraviolet dosage provided to the platelet preparation in bag 10a by gently agitating the bag so that the liquid platelet preparation swirls and moves within the bag. This provides more uniform irradiation of the cells and typically permits the use of a lower minimum dose of UV radiation necessary to decrease or eliminate the immune response to the platelet preparation by alloimmunized patients.

To accomplish this, a rotatable, eccentric cam 60 is carried within casing 42, the cam 60 being connected to a rotary motor 62, and connected to engage drawer bottom 56, typically at an edge thereof. Drawer bottom 56, in turn, is pivotally attached to the side members 52 of drawer 48 at conventional pivots 64 so that drawer bottoms 56 can pivot about pivot point 66 in a manner shown particularly in FIG. 6.

Thus, when drawer 48 is closed, the front end 68 of drawer bottom 56 rests exclusively on eccentric cam 60 within the front face and handle 50 of the drawer. In this circumstance, while irradiation takes place, eccentric cam 60 can be rotated by motor 62 to cause drawer bottom 56 to engage in back-and-forth pivoting of the drawer bottom, which results in a gentle agitation of the liquid platelet preparation, when such agitation is desired.

When drawer 48 is partially open, drawer bottom 56 may be supported by the top of front frame portion 70 so that it does not pivot downwardly in perpendicular manner. It is an easy matter to simply add or remove a bag 10a from its resting position on window 58, and then to close the drawer again, manually holding pivotable drawer bottom 56 in generally horizontal position if necessary as the drawer is closed.

The weight of the liquid platelet preparation in bag 10a tends to provide a liquid layer of generally equal thickness as it rests upon quartz window 58.

Accordingly, by this invention, a convenient and effective apparatus is provided for the ultraviolet irradiation of blood products, having advantages as described below.

The above has been offered for illustrative purposes only, and is not intended to limit the scope of the invention of this application, which is as defined in the claims below.

That which is claimed is:

1. The method of irradiating a layer of a blood product containing white blood cells with ultraviolet radiation predominately of a wavelength of 280 to 320 nanometers, to provide a total energy exposure of 800 to 20,000 millijoules per square cm. of ultraviolet radiation, whereby said white blood cells substantially lose their capability to set off an immune reaction in an alloimmunized patient.

2. The method of claim 1 in which said blood product is irradiated while occupying a flat, flexible bag made of poly(ethylene-vinyl acetate) plastic.

3. The method of claim 2 in which said plastic contains from 10 to 30 weight percent by weight of vinyl acetate units and said bag has a wall thickness of 0.005 to 0.025 inch.

4. The method of claim 1 in which said layer of blood product is from 0.1 to 5 cm. thick.

5. The method of claim 1 in which said irradiation is from 0.25 to 30 minutes long.

6. The method of claim 1 in which said blood product is irradiated while occupying a flat, flexible bag which is stretched during said irradiation to define a thin film of blood product within said bag.

7. The method of claim 1 in which the total energy exposure of ultraviolet radiation applied is 10,000 to 14,000 millijoules per square cm.

8. The method of claim 1 in which said total energy exposure is 1600 to 2500 millijoules per square cm.

9. The method of claim 1 in which the intensity of said ultraviolet radiation is 4 to 20 milliwatts per square cm.

10. The method of claim 1 in which said intensity is 10 to 15 milliwatts per square cm.

11. The method of claim 7 in which said irradiating takes place without agitation of the layer of blood product.

12. The method of claim 1 in which said ultraviolet radiation is predominately of a wavelength of 300 to 320 nanometers.

13. The method of irradiating a layer of blood product containing white blood cells with ultraviolet radiation predominately of a wavelength of 280 to 320 nanometers, which comprises: presenting said blood product to the radiation while said blood product occupies a flat, flexible bag made of poly(ethylene-vinyl acetate) plastic, said plastic containing from 10 to 30 percent of vinyl acetate units, and said bag having a wall thickness of 0.005 to 0.025 inch, to provide a total energy exposure of 800 to 20,000 millijoules per square cm. of ultraviolet radiation, whereby said white blood cells substantially lose their capability to set off an immune reaction in an alloimmunized patient.

14. The method of claim 13 in which said bag is axially stretched during said irradiation to define said thin film of blood product within said bag.

15. The method of claim 13 in which said layer of white blood cells is from 0.1 to 5 cm. thick.

16. The method of irradiating a layer of blood product containing white blood cells with ultraviolet radiation predominately of a wavelength between 280 to 320 nanometers at an intensity of 9 to 20 milliwatts per square cm., with agitation of the film, to provide a total energy exposure of 800 to 2800 millijoules per square cm. of ultraviolet radiation, in which said blood product is irradiated while occupying a flat, flexible bag which is stretched during said irradiation to define said layer of white blood cells within said bag, said bag being made of poly(ethylene-vinyl acetate) plastic.

17. The method of claim 16 which said plastic contains from 10 to 30 weight percent of vinyl acetate units, and said bag has a wall thickness of 0.005 to 0.025 inch.

18. The method of claim 16 in which said irradiation is from 10 to 30 minutes long.

19. The method of claim 16 in which said layer of white blood cells is from 1 to 4 cm. thick.

20. Apparatus for irradiating with ultraviolet radiation a layer containing white blood cells, which comprises: means for providing ultraviolet radiation predominately of a wavelength of 280 to 320 nanometers at an intensity of 9 to 20 milliwatts per square cm.; means for supporting a layer of white blood cells in a position to be irradiated by said irradiation means, and means for initiating and terminating said irradiation.

21. The apparatus of claim 20 which includes means for stretching a flat, flexible bag containing said white blood cells during said irradiation to assist in forming said layer.

22. The apparatus of claim 21, in combination with a flat, flexible bag made of poly(ethylene-vinyl acetate) plastic containing said white blood cells.

23. The apparatus of claim 22 in which said plastic contains from 10 to 30 percent by weight of vinyl acetate units, and said bag has a wall thickness of 0.005 to 0.025 inch.

24. The apparatus of claim 23 in which said layer of white blood cells is from 0.1 to 5 cm. thick.

25. Apparatus for irradiating with ultraviolet radiation a layer of blood product containing white blood cells, which comprises:
a housing; means for providing ultraviolet radiation; means for supporting in said housing a layer of white blood cells in a position to be irradiated by said irradiation means, said supporting means comprising a drawer member slideable into and out of said housing to carry an ultraviolet transmissive container which defines said layer, said drawer member defining a container-supporting ultraviolet-transmissive surface including at least part of a bottom to said drawer, said drawer bottom being pivotally attached to the remainder of said drawer member, wherein said surface permits ultraviolet radiation from said ultraviolet providing means to pass through the container-supporting surface and said container carried thereon, to irradiate said layer containing white blood cells.

26. The apparatus of claim 25 in which said drawer member is movable between an open position permitting placement and removal of said container into and out of said drawer member, and a closed position in which said container in the drawer member is positioned within said housing for ultraviolet irradiation, and elevating means positioned to cause back-and-forth pivoting of said drawer bottom while said drawer member is in said closed position, to permit agitation of said layer containing white blood cells in said ultraviolet-transmissive container carried on said drawer bottom simultaneously with ultraviolet irradiation thereof.

27. The apparatus of claim 26 in which said elevating means comprises a rotatable, eccentric cam upon which said drawer bottom rests.

28. Apparatus for irradiating with ultraviolet radiation a layer of blood product containing white blood cells, which comprises:
a housing; means for providing ultraviolet radiation; means for supporting a layer of white blood cells in a position to be irradiated by said irradiation means, said supporting means comprising a drawer member slideable into and out of said housing to carry an ultraviolet transmissive container which defines said layer, said drawer member defining a container-supporting surface, said container-supporting surface of the drawer member being pivotally attached to the remainder of said drawer member; and elevating means positioned to cause back-and-forth pivoting of said drawer bottom when the drawer member is in closed position, to permit agitation of said layer containing white blood cells in said ultraviolet-transmissive container carried on said drawer bottom simultaneously with ultraviolet irradiation thereof.

29. The apparatus of claim 28 in which said elevating means comprises a rotatable, eccentric cam upon which said drawer bottom rests.

30. Apparatus for irradiating with ultraviolet radiation a layer of blood product containing white blood cells, which comprises:
a housing; means for providing ultraviolet radiation; means for supporting in said housing a layer of white blood cells in a position to be irradiated by said irradiation means, said supporting means comprising a drawer member slideable into and out of said housing to carry an ultraviolet transmissive container which defines said layer, said drawer member defining a container-supporting ultraviolet-transmissive surface made of quartz, to permit ultraviolet radiation from said ultraviolet providing means to pass through the container-supporting surface and said container carried thereon, to irradiate said layer containing white blood cells.

31. Apparatus for irradiating with ultraviolet radiation a layer of blood product containing white blood cells, which comprises:
a housing; means for providing ultraviolet radiation; means for supporting in said housing a layer of white blood cells in a position to be irradiated by said irradiation means, said supporting means comprising a drawer member slideable into and out of said housing to carry an ultraviolet transmissive container which defines said layer, said drawer member defining a container-supporting ultraviolet-transmissive surface to permit ultraviolet radiation from said ultraviolet providing means to pass through the container-supporting surface and said container carried thereon, to irradiate said layer containing white blood cells, said means for providing ultraviolet radiation also providing said radiation directly to a side of said container facing away from the container-supporting surface.

* * * * *

Disclaimer 4,952,812—*Jeffrey E. Miripol*, Newark, Del., *Arnold Bilstad*, Deerfield, Ill., *John Foley*, Wheeling, Ill., *Dean Glash*, McHenry, Ill., *William R. Bratten*, Lake Villa, Ill. IRRADIATION OF BLOOD PRODUCTS. Patent dated Aug. 28, 1990. Disclaimer filed May 6, 1991, by the assignee, Baxter International Inc.

The term of this patent subsequent to Feb. 23, 2005, has been disclaimed.
[ *Official Gazette August 6, 1991* ]

UNITED STATES PATENT AND TRADEMARK OFFICE
CERTIFICATE OF CORRECTION

PATENT NO. : 4,952,812

DATED : August 28, 1990

INVENTOR(S) : Jeffrey E. Miripol, et al.

It is certified that error appears in the above-identified patent and that said Letters Patent is hereby corrected as shown below:

Title page: Item (63);

Amend "Related U.S. Application Data", third line, as follows:

Change "abandoned" to -- Pat. No. 4,726,949. --

Signed and Sealed this

Twenty-ninth Day of September, 1992

Attest:

DOUGLAS B. COMER

*Attesting Officer*    *Acting Commissioner of Patents and Trademarks*